United States Patent [19]
Lance-Gomez et al.

[11] Patent Number: 5,393,521
[45] Date of Patent: Feb. 28, 1995

[54] HAIR TREATMENTS UTILIZING POLYMETHYLALKYLSILOXANES

[75] Inventors: Theodore E. Lance-Gomez; Husam A. A. Rasoul, both of Racine, Wis.

[73] Assignee: DEP Corporation, Rancho Dominguez, Calif.

[21] Appl. No.: 859,701

[22] PCT Filed: Sep. 7, 1990

[86] PCT No.: PCT/US90/07154

§ 371 Date: Jun. 8, 1992

§ 102(e) Date: Jun. 8, 1992

[87] PCT Pub. No.: WO91/09586

PCT Pub. Date: Jul. 11, 1991

Related U.S. Application Data

[63] Continuation-in-part of Ser. No. 454,214, Dec. 21, 1989, abandoned.

[51] Int. Cl.$^6$ .................................................. A61K 7/09
[52] U.S. Cl. .................................... 424/70.12; 424/73
[58] Field of Search ............................. 424/71, 70, 73

[56] References Cited

U.S. PATENT DOCUMENTS

| | | | |
|---|---|---|---|
| 2,807,557 | 9/1957 | Carney | 117/141 |
| 2,826,551 | 3/1958 | Geen | 252/89 |
| 3,185,627 | 5/1965 | Kass | 167/90 |
| 3,208,911 | 9/1965 | Oppliger | 167/87 |
| 3,395,169 | 7/1968 | Mitchell | 424/60 |
| 3,641,239 | 2/1972 | Mohrlok | 424/64 |
| 3,882,824 | 5/1975 | Acquaviva | 119/156 |
| 3,964,500 | 6/1976 | Drakoff | 132/7 |
| 4,364,837 | 12/1982 | Pader | 252/173 |

(List continued on next page.)

FOREIGN PATENT DOCUMENTS

| | | |
|---|---|---|
| 57837 | 8/1982 | European Pat. Off. . |
| 59-05640 | 2/1984 | Japan . |
| 63-313714 | 12/1988 | Japan . |
| 992087 | 5/1965 | United Kingdom . |

OTHER PUBLICATIONS

"Dow Corning® 244, 245, 344 and 345 Fluids, Dow Corning® 200 Fluid, 0.65 cs.", Brochure No. 22-90-4-82, Dow Corning Corporation, Midland, Mich. 6 pgs. (1982).

"Silicone Fiber and Thread Lubricant Sf1134", Brochure from General Electric Silicones, 2 pgs. (undated).

"Organo-polysiloxanes for Cosmetic Formulations", H. J. Kollmeier.

Memo dated Dec. 4, 1991 from P. Davies of Th. Goldschmidt Ltd. on ABIL® Wax 9810/9801/9800 plus 5 pages information on ABIL® Wax 9810, 6 pages.

*Primary Examiner*—Thurman K. Page
*Assistant Examiner*—William E. Bentson, Jr.
*Attorney, Agent, or Firm*—Blakely, Sokoloff, Taylor, Zafman

[57] ABSTRACT

These improved compositions include a polymethylalkylsiloxane hair conditioning These improved compositions include a polymethyMcarrier medium such as a hair shampoo, hair conditioner or aerosol spray composition. The polymethylalkylsiloxane is from 0.1% to about 10% by weight of the total composition and is of the general formula: $R_2(CH_3)Si(OSi(CH_3)_2)_x(OSiR'CH_3)_yOSi(CH_3)R_2$, wherein each R is selected from the group consisting or methyl, ethyl and phenyl groups, R' is an alkyl group of from 8 to about 60 carbon atoms where the total number or R' groups present has an average of at least 12 carbon atoms, the values of x and y are such that the ratio of x:y is in the range of from 97:3 to 55:45, the sum of x+y is greater than or equal to about 60 and less than or equal to about 1,333 and the polymethylalkylsiloxane has a melting transition, as measured by a differential scanning calorimeter, between about −25° C. to +27° C. Also claimed is a method of conditioning the hair by applying such a composition to the hair and a method of improving the hair conditioning ability of a cosmetically acceptable hair treating composition by adding such a polymethylalkylsiloxane to such a composition.

10 Claims, No Drawings

U.S. PATENT DOCUMENTS

| | | | |
|---|---|---|---|
| 4,423,032 | 12/1983 | Abe et al. | 424/70 |
| 4,559,227 | 12/1985 | Chandra et al. | 424/70 |
| 4,563,347 | 1/1986 | Starch | 424/70 |
| 4,574,082 | 3/1986 | Tietjen et al. | 424/63 |
| 4,586,518 | 5/1986 | Cornwell et al. | 424/70 |
| 4,597,964 | 7/1986 | Ziemelis et al. | 424/70 |
| 4,601,902 | 7/1986 | Fridd et al. | 424/70 |
| 4,658,839 | 4/1987 | Dallal et al. | 132/7 |
| 4,699,780 | 10/1987 | Jennings et al. | 424/60 |
| 4,704,272 | 11/1987 | Oh et al. | 424/70 |
| 4,725,658 | 2/1988 | Thayer et al. | 528/15 |
| 4,728,457 | 3/1988 | Fieler et al. | 252/174 |
| 4,741,855 | 5/1988 | Grote et al. | 252/142 |
| 4,744,978 | 5/1988 | Homan et al. | 424/70 |
| 4,749,732 | 6/1988 | Kohl et al. | 524/43 |
| 4,902,499 | 2/1990 | Bolich, Jr. et al. | 424/70 |
| 4,936,914 | 10/1987 | Jennings et al. | 424/60 |
| 4,973,476 | 11/1990 | Krzysik | 424/71 |
| 5,100,657 | 3/1992 | Ansher-Jackson et al. | 424/70 |
| 5,106,613 | 4/1992 | Hartnett et al. | 424/71 |
| 5,114,706 | 5/1992 | Duvell | 424/70 |
| 5,169,623 | 12/1992 | Kopolow et al. | 424/70 |

HAIR TREATMENTS UTILIZING POLYMETHYLALKYLSILOXANES

This is a continuation-in-part of co-pending U.S. Ser. No. 07/454,214, filed on Dec. 21, 1989, now abandoned.

TECHNICAL FIELD

This invention relates to an improved composition for treating the hair which comprises a specific polymethylalkylsiloxane as at least one of the hair conditioning agents that are dispersed within a cosmetically acceptable carrier medium to form the composition. The invention also relates to a method of conditioning the hair which comprises applying such a composition to the hair and also to a method of improving the hair conditioning ability of a cosmetically acceptable hair treating composition by adding such a polymethylalkylsiloxane to the hair treating composition.

BACKGROUND ART

Silicone polymers such as those having the Cosmetic Toiletries and Fragrance Association Adopted Names of "dimethicone" (i.e., trimethylsiloxy-endblocked polydimethylsiloxanes) and "cyclodimethicone" (i.e., polydimethylcyclosiloxanes) have been used in cosmetic formulations for the hair such as shampoos and hair conditioners to enhance the gloss, sheen and drying time of the hair. Because of their silicone nature, these compounds also lubricate the hair and make it easier to comb. However, use of an excessive amount of silicone polymer can result in hair which has a coated or greasy appearance. The relatively short methyl groups attached to the silicon atoms in polydimethylsiloxanes enhance the character of the polymer. Polydimethylsiloxanes are also relatively insoluble in water and in many water-containing solvents.

To provide a blend of silicone character and substantive hair conditioning properties, silicone organic polymers containing amine-, quaternary- or carboxy-functional groups extending from the silicon atoms forming the backbone of the polymer have been proposed as can be seen from U.S. Pat. Nos. 4,563,347 to Starch (polyorganosiloxanes having functional substituents providing attachment to the hair where the alkyl substituents can have 1–8 carbon atoms); 4,586,518 to Cornwall et al. (hair setting using aminoalkyl-substituted polydiorganosiloxanes); 4,559,227 to Chandra et al. (conditioning shampoos with amine-functional polydiorganosiloxanes); 4,744,978 to Homan et al. (hair treatments using carboxy-functional polydimethylsiloxanes and a cationic, organic polymer); 4,601,902 to Fridd et al. (hair treatments using silanes or polydiorganosiloxanes having quaternary ammonium groups along with amine-functional polydiorganosiloxanes) and 4,597,964 to Ziemelis et al. (hair treatments with cationic polydiorganosiloxanes) and 4,749,732 to Kohl et al. (hair care compositions employing polydiorganosiloxanes containing aminoalkyl groups modified by alkoxycarbonylalkyl groups). Thus, there has been a trend to employ silicone polymers which contain functional groups to treat and condition the hair.

Column 1 of the '732 Patent states that the addition of functional groups to polydiorganosiloxanes has a disadvantage in that the chemical reactivity of aminoalkyl groups may present a problem in regard to compatibility with other common components of hair care formulations.

Other types of polyorganosiloxane polymers have been used in conjunction with the treatment of furs and hair as well as textiles.

British Pat. No. 992,087 to Dow Corning Corporation teaches a process for treating hair with an aqueous emulsion of an organosiloxane polymer having an average of from 1.9 to 2.1 organic radicals per silicon atom in the polymer. The silicon-bonded organic radicals are selected from monovalent hydrocarbons and halogenated hydrocarbons such as methyl, ethyl and octadecyl, vinyl, cyclohexyl, phenyl, chlorophenyl and 3,3,3-trifluoropropyl and can even include hydrogen although methyl radicals are preferred. The emulsions are said to be especially useful for rinsing the hair after shampooing to improve the manageability of the hair and to impart a marked softness and feeling of silkiness to the touch.

U.S. Pat. No. 2,807,557 to Carney teaches a method of treating furs, preferably using a combination of an polyorganosiloxane resin and a polyorganosiloxane oil in an oil-in-water emulsion. The alkyl radical in the polyorganosiloxane oil can be methyl, ethyl propyl or octadecyl. These compositions are said to improve the luster and the general feel of fur treated with them.

U.S. Pat. No. 3,208,911 to Oppliger teaches a method for treating hair with ionic oil-in-water emulsions of polyorganosiloxanes to get more gloss and shine as well as superior manageability and a soft feel. Column 2, lines 9–10 teach that the R group in the formula given can be methyl or octadecyl. A wide range of viscosities for the silicone compounds is given, with 10–10,000 centistokes ($1 \times 10^{-5}$ to $1 \times 10^{-2}$ square meter per second) being preferred.

U.S. Pat. No. 3,185,627 to Kass teaches the use of a solvent to make incompatible silicones compatible with cosmetic ingredients. Column 4, lines 10–12 teach that some examples of useful silicones are laurylmethylsiloxane fluid (DC 1300 Fluid) and dilaurylpolysiloxane fluid (DC 1500 Fluid).

U.S. Pat. No. 3,882,824 to Acquaviva teaches a hair polish composition comprising a liquid silicone which can be applied to the coat of an animal and will later dry to the desired superior shiny finish. It teaches the use of polyalkylsiloxanes although dimethylpolysiloxanes are specifically taught to be useful. Column 4, lines 44–45 teach that while the compositions can be used for hairy animals, it also states that wigs made from humans can be treated to provide the improved shiny finish.

U.S. Pat. No. 4,423,032 to Abe et al. teaches hair treatments composed of keratin decomposition products and certain derivatives based on polyorganosiloxanes. Useful silicone derivatives are described in columns 6 and 7, particularly the alkyl-modified silicone oils which are described in column 7, lines 12–38.

U.S. Pat. No. 4,574,082 to Tietjen et al. teaches one-phase silicone-based cosmetic products containing wax. The wax is mixed with a silicone material which can contain an R group that can be methyl or octadecyl. Examples A and B in column 5 employ polymethyloctadecyl siloxane. These formulations are called "foundations" which appear to be formulations for a facial cosmetic rather than a hair treatment. The compositions taught are in stick, cake or cream form.

None of the above patents describe the specific polymethylalkylsiloxanes which are employed in the present invention. Further patents showing the state-of-the-art concerning the inclusion of silicone materials in various compositions such as shampoos and conditioners as well as other cosmetic compositions are U.S. Pat. Nos. 4,658,839 to Dallal et al.; 4,364,837 to Pader; 3,964,500 to Drakoff; 4,704,272 to Oh et al.; 4,728,457 to Fieler et al.; 3,641,239 to Mohrlok and 4,725,658 to Thayer et al.

SUMMARY DISCLOSURE OF INVENTION

The present invention resides in the discovery that certain polymethylalkylsiloxanes can provide hair with improved shine and gloss as well as superior manageability and a soft feel in the same manner as polydimethylsiloxanes, but which also leave the hair feeling less coated and greasy in appearance. Relative to polydimethylsiloxane fluids, the polymethylalkylsiloxanes of the present invention also leave the hair with more body, fullness and softness. A further advantage is that the hair detangles and combs easier when dry. The hair feels less coated and has less tendency to flyaway.

These and other objects and advantages of the present invention are provided by an improved composition for treating the hair which comprises a hair conditioning agent dispersed within a cosmetically acceptable carrier medium which can be an aqueous medium. The improvement comprises including from about 0.1% to about 10%, more preferably from about 0.1% to 5%, and most preferably from about 0.5% to 2.5%, by weight of the composition, based on the total weight of the hair conditioning agents and carrier medium, of a polymethylalkyl siloxane having the average formula $$R_2(CH_3)Si(OSi(CH_3)_2)_x(OSiR'CH_3)_yOSi(CH_3)R_2$$

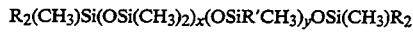

wherein each R is selected from the group consisting of methyl, ethyl and phenyl groups, preferably R is a methyl group, and each R' is an alkyl group of from 8 to about 60 carbon atoms where the total number of R' groups present has an average of at least 12 carbon atoms, and preferably an average of from 16 to 24 carbon atoms. The values of x and y are such that the ratio of x:y is in the range of from 97:3 to 55:45, more preferably from about 96:4 to 80:20, the sum of x+y is greater than or equal to about 60 and less than or equal to about 1,333, more preferably between about 250 and 800, and the polymethylalkylsiloxane has a melting transition, as measured by differential scanning calorimeter, between about −25° C. to +27° C. In such improved compositions, the polymethylalkylsiloxane can be the sole hair conditioning agent or can be one of several present in the composition.

The carrier medium can be an aqueous hair shampoo composition containing detergents such as anionic surfactants; an aqueous hair conditioner such as an emulsion containing cationic surfactants; or a carrier medium in the form of an aerosol spray composition which contains one or more solvents in addition to the polymethylalkylsiloxane of the present invention, optionally, along with a propellant, to produce an aerosol spray composition for treating the hair.

The present invention also relates to a method of conditioning hair which comprises the step of applying to the hair a composition containing from about 0.1% to about 10% by weight, based upon the total weight of the composition, of the above polymethylalkylsiloxanes dispersed in a cosmetically acceptable carrier medium.

Finally, the present invention further relates to a method of improving the hair conditioning ability of a cosmetically acceptable hair treating composition which comprises at least one hair treating agent dispersed in a carrier medium such as a hair shampoo, conditioner or aerosol spray composition, wherein the method comprises adding to that composition a polymethylalkylsiloxane of the type described above.

BEST MODE FOR CARRYING OUT THE INVENTION

The polymethylalkylsiloxane employed in the compositions and method of the present invention has the average formula $$R_2(CH_3)Si(OSi(CH_3)_2)_x(OSiR'CH_3)_yOSi(CH_3)R_2 \quad (I)$$

wherein each R is selected from the group consisting of methyl, ethyl and phenyl groups with methyl being preferred. In that formula, R' is an alkyl group of from 8 to about 60 carbon atoms which can be octyl, decyl, dodecyl, tetradecyl, hexadecyl, octadecyl, eicosyl, docosyl, hexacosyl, octacosyl, triacontyl, tetratriacontyl, hexatriacontyl, octatriacontyl, tetracontyl, dotetracontyl, tetratetracontyl, hexatetracontyl, octatetracontyl, pentacontyl, dopentacontyl, tetrapentacontyl, hexapentacontyl, octapentacontyl and hexacontyl. Although branched chain alkyl groups can be employed, it is preferred that the alkyl groups be linear since the organic character of these alkyl groups is what contributes to the effectiveness of the polymethylalkylsiloxanes in the compositions of the present invention. The organic character modifies the silicone character imparted by the siloxane units present in the back bone of the polymethylalkylsiloxanes by permitting those groups to associate with hydrophobic materials. To provide sufficient organic character to the polymethylalkylsiloxane, the total number of R' groups and the number of carbon atoms contained therein is selected so that the average number of carbon atoms in all R' groups present is at least 12. Below an average of 12 carbon atoms in the total R' groups present, the overall hair treating performance of compositions containing such polymethylalkylsiloxanes decreases. Therefore, it is even more preferred that the average number of carbon atoms in the total R' groups present be at least 16 and most preferably between 16 and 24 carbon atoms.

The polymethylalkylsiloxanes used in the present invention are made according to conventional procedures which are well known to those of ordinary skill in the preparation of polydiorganosiloxanes. The backbone prepolymers are prepared according to conventional methods involving the equilibration of dimethylsiloxanes and organosilanes or organosiloxanes containing at least one silicon hydride unit such as methyldichlorosilane or 1,2,3,4-tetramethylcyclotetrasiloxane in the presence of a basic catalyst. Polyorganosiloxanes containing dimethylsiloxane units as well as methylhydridesiloxane units are also commercially available from various sources such as the General Electric Company, Silicone Products Division of Waterford, N.Y. and the Dow Corning Corporation of Midland, Mich.

Using conventional and well-known techniques, 1-alkenes can be added to the silicon hydride-functional polyorganosiloxane prepolymer through the platinum-catalyzed addition of such alkenes to the hydride group. Thus, a polymethylalkylsiloxane of the present invention containing an R' group with 18 carbon atoms can be obtained by the platinum-catalyzed addition of 1-octadecene to a polyorganosiloxane prepolymer which is a trimethylsiloxy-endblocked copolymer of dimethylsiloxane units and methylhydridesiloxane units. To obtain alkyl groups with an average of more than 20 carbon atoms, it is generally more economical to use mixtures of these higher 1-alkenes. A typical mixture is a mixture of $C_{30}+$ 1-alkenes is described in U.S. Pat. No. 3,553,177. Another commercially available mixture of higher 1-alkenes is a mixture of $C_{20}$ to $C_{24}$ 1-alkenes. It is preferred that the higher 1-alkenes be essentially monoolefinic since diolefins can cause gel formation and cross-linking. Another commercially available source of 1-alkenes is that containing a mixture of $C_{24}$–$C_{28}$ 1-alkene mixtures. The 1-alkenes are commercially available from Ethyl Corporation of Baton Rouge, La. and Chevron Chemical Company of Houston, Tex.

In Formula I above, the polymethylalkylsiloxane is composed of units of polydimethylsiloxane randomly interspersed with methylalkylsiloxane units where the alkyl group corresponds to the R' group noted above. Because the polymers are typically prepared by an equilibration method, the polymers are composed of an average number of each such unit. To obtain good performance in treating the hair, there must be a minimum number of each type of unit to balance the essentially siloxane character of the polydimethylsiloxane units against the more hydrophobic organic character of the methylalkylsiloxane units. Thus the ratio of x:y should be in the range of from about 97:3 to 55:45. In a more preferred embodiment, each R' is selected from linear alkyl groups having an overall average from 16 to 24 carbon atoms. More preferably, R is a methyl group. In such compositions, it is preferred that the ratio of x:y be from 96:4 to 80:20.

In a still more preferred embodiment, the ratio of x:y is from 97:3 to 93:7 so that the polymethylalkylsiloxane has sufficient siloxane character contributed by the polydimethylsiloxane units to offset the organic character contributed by the methylalkylsiloxane units. These polymethylalkylsiloxanes would find utility in formulations used to treat normal hair since they have less alkyl content.

On the other hand, for dry hair or hair damaged by bleaching, permanent waving, heat, etc., compositions employing a higher alkyl content can be employed such as those where the ratio of x:y is from 88:12 to about 80:20. The amount of polysiloxane hair conditioning agent in that case ranges from 0.1% to 5% by weight of the composition with from 0.5% to 2.5% being more preferred.

Thus, the ratios of the organosiloxane units present can be altered to suit the needs of the particular hair which the hair treating composition is designed to treat.

To be effective, the sum of $x+y$ should be greater than about 60 and less than or equal to about 1,333. A very low molecular weight polymethylalkylsiloxane will have too little silicone character to condition the hair. A very high molecular weight polymer will tend to be difficult to synthesize as well as being too high in viscosity and will lose the fluid or gel-like character that we find contributes to the hair conditioning ability of the polymethylalkylsiloxanes used in our invention.

In addition to a molecular weight limitation, the polymethylalkylsiloxanes of the present invention must also have a melting transition, as measured by a differential scanning calorimeter, between about $-25°$ C. to $+27°$ C. Polymethylalkylsiloxanes falling outside of this range do not have all of the advantageous properties possessed by those falling within this range. For example, polydimethylsiloxane fluid of weight average molecular weight greater than about 2000 in weight average molecular weight has a transition that is less than $-30°$ C. Polymethylalkylsiloxanes of Formula (I) above generally have a melting transition which is outside of this range when the total average carbon chain length of the R' groups present falls below 12. Differential scanning calorimeters are well known in the art and are available from sources such as the DuPont 910 Differential Scanning Calorimeter from E.I. DuPont de Nemours & Co., Instrument Products Division, of Wilmington, Del. used in the following examples.

A further requirement for utility in the present invention is that the polymethylalkylsiloxane be in the form of a fluid or a gel-like material rather than a solid or a wax at room temperature or a very low viscosity fluid. Polymethylalkylsiloxanes meeting the above requirements will be in the form of the desired fluid or gel-like material at room temperatures.

The above polymethylalkylsiloxanes act as hair conditioning agents and can be dispersed within a cosmetically acceptable carrier medium. The term "cosmetically acceptable" is intended to mean that it is suitable for contact with the human body and, more specifically, in conjunction with human hair. As is well known in the art, an aqueous carrier medium is typically used and the polymethylalkylsiloxanes of the present invention can be used in hair shampoos such as those taught in U.S. Pat. No. 4,321,156 to Bushman which comprises an anionic detergent and inorganic salt, a pH adjusting amount of an acid and water. As is well known in the art, shampoos for the hair can include anionic surfactants such as sodium and ammonium lauryl sulfate and sodium and ammonium lauryl ether sulfates, fatty alkyl ether carboxylates and fatty alkyl ether sulfosuccinates; nonionic surfactants such as fatty alkyl ethers and sorbitan esters of fatty acids; amphoteric surfactants such as fatty alkyl betaines, sulfobetaines and imidazolines and, in some cases, cationic surfactants such as fatty alkyl amidoamines and fatty alkyl quaternary ammonium compounds. The term "fatty alkyl" is intended to mean a long chain alkyl radical having from about 12 to 22 carbon atoms.

In shampoos, the polymethylalkylsiloxane can be the sole hair conditioning agent present in the composition. It is possible that other conventional hair conditioning agents such as organic cationic hair conditioning agents could be added to the shampoos. However, it is more common to have a cationic hair conditioning agent present in a composition wherein the carrier medium is a hair conditioner which can be used as a leave-on treatment or it can be rinsed off the hair. For example, polymethylalkylsiloxanes of the present invention could be added to a cream rinse conditioner of the type described in U.S. Pat. No. 4,421,740 to Burton which comprises an aqueous emulsion of cetyl alcohol and a fatty alkyl quaternary ammonium compound as a cream rinse product. It is placed on the hair after shampooing, allowed to remain on the hair for a period of time, and is then rinsed away. Examples of conditioning compounds employed in the '740 compositions are stearyl dimethyl benzyl ammonium chloride and cetyl dimethyl amine oxide. A further ingredient is a thickener or protective colloid which can be hydroxyethylcellulose or guar gum. Other examples of suitable hair conditioner carrier media will be apparent to those of ordinary skill in the art.

Another example of a carrier medium is a composition which is dispensed from an aerosol container in the form of a collapsible foam aerosol hair product often called a "mousse" product. The foam produced from a mousse product readily collapses onto the hair after dispensing upon being touched or mechanically agitated. One such foam mousse product is described in U.S. Pat. No. 4,536,390 to Padden and comprises from 3 to 95% by weight of a Volatile propellant such as propane or butane and from 97 to 10% by weight of an aqueous intermediate containing from 0.25 to 2% by weight of a quaternary ammonium compound conditioning agent such as cetyltrimethyl ammonium chloride as well as from about 0.25 to 5% of a high molecular weight polymer selected from the group consisting of cationic polymers, amine functional polymers and mixtures thereof with the balance being water and wherein the composition contains less than 10% of an alcohol having from one to four carbon atoms.

Another example of a carrier medium which can be used to treat hair with polymethylalkylsiloxanes of the present invention is to use a cosmetically acceptable solvent such as ethanol as an aerosol spray carrier medium and to spray a low viscosity solution of the polymethylalkylsiloxane on the hair. Other examples of solvents are isoproponol, volatile polydimethylsiloxane and polydimethylcyclosiloxane fluids, and other solvents commonly used in hair spray formulations which are compatible with the polymethylalkylsiloxane chosen. These types of compositions can then be applied to the hair using a conventional pump spray container.

If a self-pressurized aerosol spray is desired, then conventional propellants such as volatile hydrocarbons such as n-propane, isopropane, n-butane and isobutane can be used as well as compressed gasses such as nitrogen and carbon dioxide. In some cases, the hydrocarbon propellants can act as the solvent for the polymethylalkylsiloxane. These compositions are packaged in conventional aerosol containers having an aerosol valve and an actuator button to permit dispensing as a self-pressurized aerosol spray.

Other carrier media will be apparent to those of ordinary skill in the art. It will be readily apparent that the type and amount of polymethylalkylsiloxane employed must be such that the compositions remain stable and do not separate into several phases which would cause them to be more difficult to apply evenly to the hair. Conventional dispersing aids may be used to improve the compatibility of the polymethylalkylsiloxane with a specific composition. Examples of such aids are certain long chain ($C_{16}$ to $C_{22}$) acyl compounds of the type described in U.S. Pat. No. 4,741,855 to Grote, et al. One advantage of the use of the polymethylalkylsiloxanes of the present invention is that they are more compatible with compositions containing organic groups because they contain long chain alkyl groups. As a result, these polymethylalkylsiloxanes are capable of treating the hair and are somewhat more compatible in hair treating compositions than the corresponding polydimethylsiloxanes of the same average molecular weight.

As will be appreciated by those of ordinary skill in the art, the carrier media in which the polymethylalkylsiloxanes of the present invention are dispersed can further contain optional ingredients of the types normally used in shampoos, hair conditioning compositions, mousses and the like. For example, fragrances, antioxidants, vitamins, thickening agents, cosmetically acceptable solvents, preservatives, dyes, inorganic salts for viscosity control, and the like which are commonly employed in such compositions can be included in compositions of the present invention in amounts which are generally less than about 5% of the total composition.

INDUSTRIAL APPLICABILITY

Thus, the carrier media employed to deliver the polymethylalkylsiloxane of the present invention can range from shampoos, hair conditioners such as cream rinses and leave-on products, mousse products and hairsprays. One advantage of the present invention is that the amounts of the polymethylalkylsiloxanes as well as the ratio of the polydimethylsiloxane units to the methylalkylsiloxane units can be altered so that various types of hair can be treated with good results.

As part of the total composition, from about 0.5-7% is preferred with 0.5-5% being more preferred and most preferred is. 0.5-2.5% polymethylalkylsiloxane based upon the total composition in percent by weight. For use with normal hair, it is preferable to use polymethylalkylsiloxanes having lower alkyl content such that the ratio of x:y is from 97:3 to 93:7. In the polymethylalkylsiloxanes of the present invention, higher alkyl content could give treated hair a greasier appearance.

Thus for dry hair, the use of polymethylalkytsiloxanes having a higher alkyl content is more desirable such as where the ratio of x:y is from 88:12 to 80:20. The polymethylalkylsiloxanes hair conditioning agent is from 0.1% to 5% by weight of the composition with from about 0.5% to about 2.5% being more preferred. Dry hair or damaged hair requires the replacement of oils which are either naturally deficient from a person's hair or were removed during previous shampooing or other hair treatments. It thus benefits from treatment with the polymethylalkylsiloxanes of the present invention.

Thus, one aspect of the present invention is a method of treating the hair through the application of the polymethylalkylsiloxanes of the present invention to the hair by means of a shampoo, hair conditioner, mousse, aerosol spray, or other carrier media. The polymethylalkylsiloxane does not have to be the only hair conditioning agent present. Conventional hair conditioning agents such as quaternary ammonium compounds can be further included to provide specific benefits to the hair. Because of the quaternary ammonium groups present in the organic cationic hair conditioning agents, they will tend to be more substantive to the hair than the essentially nonpolar polymethylalkylsiloxanes of the present invention. In this manner, a synergistic effect can be obtained where the benefits of the siloxane polymer enhance the benefits obtained by an organic hair conditioning agent.

The polymethylalkylsiloxanes of the present invention can thus improve the properties of a cosmetically acceptable hair treating composition such as a conventional hair shampoo, hair conditioner or aerosol formulation.

The following Examples are provided to show various aspects of the present invention without departing from the scope and spirit of the invention. Unless otherwise indicated, all parts and percentages used in the Examples are by weight. In the Examples, the molecular weights were measured by Gel Permeation Chromatography using polystyrene molecular weight standards. "Room temperature" is between 20° C. and 25° C.

Example 1

This Example demonstrates the production of a hair conditioner composition containing a polymethylalkylsiloxane of the present invention which is applied to the hair and then rinsed off with water.

A polymethylalkylsiloxane was conventionally prepared by the platinum-catalyzed addition of 1-octadecene to a trimethylsilyl-endblocked copolymer of dimethylsiloxane and methylhydridesiloxane units to obtain a polymer of the type shown in Formula I, supra, wherein R was a methyl group, R' was an octadecyl group, x had an average value of 400 and y had an average value of 18. The weight average molecular weight of the resulting polymer was 56,974 and it had a number average molecular weight of 3,157 with a peak molecular weight of 36,627. This polymer was a viscous liquid at room temperature, had a melting transition as measured by the DuPont 910 Differential Scanning Calorimeter of −15.4° C., and will be referred to as "Silicone I".

Silicone I was used in the preparation of the hair conditioner formulation described in Table I below.

TABLE I

| | |
|---|---|
| Cetyl Alcohol | 2.00 |
| ADOGEN ® 432ET[1] | 0.70 |
| Citric Acid | 0.05 |
| SCHERCODINE ® S[2] | 0.40 |
| Tricetyl Amine | 0.40 |
| Silicone I | 0.50 |
| KATHON ® CG[3] | 0.032 |
| Fragrance | 0.50 |
| Ammonium Chloride (20% in water) | 1.25 |
| Deionized Water | 94.168 |
| | 100.00% |

[1]Dicetyl dimethyl ammonium chloride in ethanol at 67–69% solids from Sherex Chemical Co., Inc. of Dubbin, OH.
[2]Stearamidopropyl Dimethylamine from Scher Chemicals, Inc., of Clifton, NJ.
[3]5-Chloro-2-methyl-4-isothiazolin-3-one from Rohm and Haas Company of Philadelphia, PA.

To prepare this composition, the deionized water is heated to 76.67° C. (170° F.). The cetyl alcohol is then added with slight agitation and permitted to dissolve. The following ingredients are then added in order with time being given for each to dissolve before the next ingredient is added: ADOGEN ® 432ET, citric acid, tricetyl amine and SCHERCODINE ® S. The mixture is cooled to 37.78° C. (100° F.) and the following are added in order with agitation: Silicone I, fragrance and KATHON ® CG. The formulation is then cooled to room temperature and then mixed in a high shear mixer (IKA Works ULTRA-TURRAX ® T50 high shear rotary mixer from IKA Works of Staufen, West Germany with an S50-G45G generator and shaft at 4,000–10,000 R.P.M.) until the formulation has a thick creamy appearance. The ammonium chloride solution is then added with mixing until a viscosity of from 3,000–7,000 centipoise (3–7 pascal seconds) is reached.

To use the resulting hair conditioner composition, the user is instructed to shampoo the hair and squeeze out excess water. A generous amount of the hair conditioner composition is then worked through the hair. The hair conditioner composition is then rinsed thoroughly from the hair with water and the hair is then set as usual.

Example 2

In this Example, the ability of Silicone I to act as a hair conditioning agent by itself was evaluated using two trained hair stylists who applied an aerosol spray composition containing Silicone I to the hair of a panel of 14 women volunteers.

The aerosol spray composition used was composed of 2% Silicone I, 49% SF-1202 Silicone Fluid (principally decamethylcyclopentasiloxane from General Electric) and 49% SD Alcohol 3A (190 proof ethanol denatured with methyl alcohol). A number of standard 202×509 lined tin-plated steel aerosol containers were filled with 100 grams each of this composition and then sealed with a Seaquist NC-31 0.013″ (0.033 cm) aerosol container valve from Seaquist Pumps, division of Pittway Corporation, of Cary, Ill. Each sealed container was pressurized through the valve using about 65 milliliters (36 grams) of isobutane as a propellant. The actuator button used on the valve was an EXCEL-100 Misty button with an orifice size of 0.013″ (0.033 cm) misty from Seaquist.

The composition from the pressurized containers was sprayed-onto the hair of 14 volunteer panelists by trained hair stylists just after each panelist's hair had been shampooed and was still wet. The composition was left on the hair while it was it was combed and detangled followed by blow drying and styling.

The stylists were asked to evaluate various aspects of the treated hair by how they rated statements such as "wets easily", "easily combed" "feels coated" "feels conditioned" and the like as applying to the treated hair using a rating scale of from 1 to 5 for both wet and dry hair as well as after the hair was dry and styled. The panelists were asked for a verbal evaluation of their hair after styling.

The results of the testing were that the spray was relatively highly rated by both the hair stylists and the panelists. Silicone I was judged to be very good for conditioning without a loss of body, fullness, or bounce. The product was not judged to leave the hair matted flat or weighted down in appearance. The dry treated hair was soft, silky and its shine was greatly enhanced. After styling, the curls on the treated side were tight with good to excellent spring.

The conditioning benefits were less noticeable for some panelists who didn't need a conditioner. In that case, the addition of the polymethylalkylsiloxane to the hair possibly resulted in overconditioning. In such cases, the curling iron used in styling may not have been able to grip the hair because the polymethylalkylsiloxane rendered the hair relatively frictionless.

One negative noted during testing was an objectionable odor presumably caused by the ethanol present. This can be overcome by simply substituting SF-1202 Silicone Fluid (principally decamethylcyclopentasiloxane) or SF1173 Silicone Fluid (principally octamethylcyclotetrasiloxane) from General Electric in place of the ethanol in the composition.

Examples 3–7

In these Examples, a liquid and a gel form of the polymethylalkylsiloxanes of the present invention were compared to each other. Liquid polymethylalkylsiloxanes were also compared to a liquid polydimethylsiloxane. They were tested for effectiveness as a hair conditioning agent in a hair conditioning carrier medium when applied to the hair of a panel of women volunteers. The panelists used in these tests had a variety of hair types ranging from normal to dry to slightly damaged due to hair dyeing, bleaching, etc.

The liquid polymethylalkylsiloxane used (hereinafter "Silicone II") was conventionally prepared by the platinum-catalyzed addition of 1-eicosene to a trimethylsilyl-endblocked copolymer of dimethylsiloxane and methylhydridesiloxane units to obtain a polymer of the type shown in Formula I, supra, wherein R was a methyl group, R' was an eicosyl group, x had an average value of 273 and y had an average value of 13. The weight average molecular weight of the copolymer prior to addition of the 1-eicosene was 20,971 and it had a number average molecular weight of 2,115. Silicone II was a medium to high viscosity liquid at room temperature and had a melting transition as measured by the DuPont 910 Differential Scanning Calorimeter of 13° C.

The gel polymethylalkylsiloxane used (hereinafter "Silicone III") was conventionally prepared by the platinum-catalyzed addition of 1-eicosene to a trimethylsilyl-endblocked copolymer of dimethylsiloxane and methylhydridesiloxane units to obtain a polymer of the type shown in Formula I, supra, wherein R was a methyl group, R' was an eicosyl group, x had an average value of 222 and y had an average value of 41. The weight average molecular weight of the copolymer prior to addition of the 1-eicosene was 18,867 and it had a number average molecular weight of 1,804. Silicone III was a gel (thick and waxy) at room temperature and had a melting transition as measured by the DuPont 910 Differential Scanning Calorimeter of 25° C.

The liquid polydimethylsiloxane was a trimethylsiloxy-endblocked polydimethylsiloxane with a viscosity of 500 centistokes ($5 \times 10^{-4}$ square meter per second) viscosity at room temperature (DOW CORNING ® 200 Fluid, 500 centistoke from Dow Corning) and is hereinafter referred to as "Silicone IV", a comparative example material.

Hair conditioning compositions were prepared by first preparing a hair conditioner base of 4% JORDAQUAT ® JWX-25 (Stearalkonium Chloride at 25% actives from Mazer Chemicals, Inc. of Gurnee, Ill.), 1% NATROSOL 250 }HR (hydroxyethylcellulose from Aqualon Company of Wilmington, Del.) and 95% deionized water (hereinafter "Base 1"). One part of Silicone II, Silicone III and Silicone IV, respectively, was dispersed into 100 parts of Base 1 using a TEKMAR RW20 DZM rotary mixer with a 4-blade stirrer from IKA Works of Staufen, West Germany at 250 to 2,000 R.P.M. to form Examples 3, 4 and 5, respectively.

A "half-head" procedure was used in this evaluation. Two trained hair stylists shampooed the entire head of each of 13 volunteer panelists and then rinsed the shampoo from the panelist's hair. The stylists then applied a measured amount of Example 3 to the hair on one side of a panelist's head using a syringe. The stylist immediately worked the conditioner into the hair on that side of the head and then rinsed it immediately from the hair using tap water. The same procedure was used on the hair on the opposite side of the panelist's head, but Example 4 was used on that side.

The identity of each polymethylalkylsiloxane was not revealed to either the hair stylist or the panelists. The hair stylist was given an evaluation form giving statements of the type noted in Example 1 above and told to evaluate the wet, dry and after-styling characteristics of the treated hair on each side of the panelist's head by ranking those statements using a scale of 1 to 5. Before the panelist left the salon, she was also given a take-home evaluation form which she was asked to complete the next morning and to telephone the results to the test facility.

Due to the small sample sizes used in the salon testing reported in most of the Examples herein, the differences in scale rankings were often small due to averaging. However, significant physical properties were noticeable upon visual inspection. Based on the results of this testing, Example 3 (liquid polymethylalkylsiloxane) was not judged to be superior to Example 4 (gel polymethylalkylsiloxane), but both delivered very good to excellent performance on key conditioner performance attributes.

The results of the hair stylists' and panelists' evaluation was that hair treated with Example 3 received higher average ratings on the following characteristics than that treated with Example 4: HAIR STYLISTS: feels less coated when wet; detangles and combs easier when dry; weighs hair down less (dry); feels softer, smoother and more conditioned; leaves hair more manageable, cleaner looking, and with more shine; and PANELISTS (next day evaluation): slightly more easily combed with less flyaway; feels less coated; leaves hair more manageable, cleaner looking and with more body and shine.

The results of the hair stylists' evaluation was that hair treated with Example 4 received higher average ratings in the following characteristics than that treated with Example 3: less flyaway; feels less dry; and less matted/flat.

The same "half-head" procedure was then repeated on a different day by two hair stylists on 17 volunteer panelists. Example 3 was placed on the hair on one side of the panelist's head and Example 5 was placed on the other side. Example 3 was found to have definite performance advantages over the comparative polydimethylsiloxane-containing Example 5. The results of the hair stylists' and panelists' evaluation was that hair treated with Example 3 received higher average ratings in the following characteristics than that treated with Example 5: HAIR STYLISTS: feels less coated when wet and dry; weighs hair down less (dry); leaves hair more manageable with more body, fullness, bounce and shine; and PANELISTS (next day evaluation): feels less coated with less flyaway; feels soft; leaves hair more manageable with more body. Example 5 was very slightly superior to Example 3 in that it was more easily combed when wet and felt more conditioned when dry according to the stylists.

Example 6 was prepared using Silicone V in the same manner as described for Example 3 and was evaluated using the half-head procedure described above versus comparative Example 7 was prepared using Silicone VI in the same manner as described for Example 5. Essentially the same results as were reported #or Example 3 versus Example 5 were obtained. Example 6 was superior to Example 7 in the same attributes noted for Example 3 over Example 5 above except the stylists reported that the manageability of the hair after styling was essentially the same for both Examples 6 and 7 and the panelists reported that the flyaway for both Examples 6 and 7 was equivalent.

Silicone V was conventionally prepared by the platinum-catalyzed addition of 1-octadecene to a trimethylsilyl-endblocked copolymer of dimethylsiloxane and methylhydridesiloxane units to obtain a polymer of the type shown in Formula I, supra, wherein R was a methyl group, R' was an octadecyl group, x had an average value of 800 and y had an average value of 36.

The weight average and number average molecular weights of the polymer could not be measured because the polymer crosslinked prior to the time that measurements were to be taken. Silicone V was a medium to high viscosity liquid at room temperature shortly after it was made and evaluated as a hair conditioning agent and had a melting transition as measured by the DuPont 910 Differential Scanning Calorimeter of $-14.1°$ C. Upon storage at room temperature, it eventually crosslinked into a gel.

Silicone VI was SF-96-100 Silicone Fluid from General Electric which was a trimethylsiloxy-endblocked polydimethylsiloxane fluid of 100 centistoke ($1 \times 10^{-4}$ square meter per second) viscosity at room temperature.

Examples 8–11

In these Examples, the hair conditioning effect of a series of polymethylalkylsiloxanes having the same backbone polymer, but different alkyl chain lengths, was instrumentally measured.

The base silicone prepolymer used was a copolymer of the type shown as Formula I, supra, where R was a methyl group, x had an average value of 273, y had an average value of 13, R' was hydrogen, the weight average molecular weight was 20,971, the number average molecular weight was 2,115 and the percent SiH content was $0.64$ mol/g $\times 10^{-3}$. Silicones VII VIII, IX and X, respectively, were prepared by the platinum-catalyzed addition of 1-octene, 1-decene, 1-dodecene and 1-eicosene, respectively, to that prepolymer.

Silicones VII, VIII and IX were each relatively low viscosity liquids at room temperature. Silicone X was a medium to high viscosity liquid at room temperature and had a melting transition as measured by the DuPont 910 Differential Scanning Calorimeter of 13° C.

Comparative Example 8 was prepared by adding 0.5% of Silicone VII to Base 1 as described for Examples 3–7. Examples 9–11, respectively, were prepared in the same manner by adding 0.5% of Silicone VIII, IX and X, respectively, to Base 1. Example 9 was also a comparative example.

The first test done was a body test which used clean dry swatches of DeMeo European Virgin Hair from DeMeo Brothers of New York, N.Y., 8 inches (20.3 cm) long weighing about 10 grams each. Five swatches were used to evaluate each of Examples 8–11.

To obtain a base hair volume reading, each swatch was shampooed and rinsed with tap water. The water was squeezed out between the fingers and the swatch was hung on a rack to air dry over a 5 hour period at room temperature. Each swatch was periodically combed and carefully brushed while it was drying to give the swatch a concentric cone shape.

After drying, the swatch was hung on a rotatable hook in front of a videocamera. The videocamera was interfaced with computer analysis equipment to allow the cross-sectional area of the swatch to be calculated from two images which is directly related to the volume of the hair swatch and calibrated using a standard size image. A videocamera image of each swatch was taken from the front and then at 90 degrees from the front. The computer generated a cross-sectional area measurement for each of the two images.

The next day, each tress was again wet with water. Two milliliters of the conditioner to be tested was applied to the swatch and worked into the hair. The conditioner was then rinsed out with tap water and brushed and combed while air drying as described above. After drying, the cross-sectional area of the tress was again measured using the above videocamera imaging method. The cross-sectional area obtained was subtracted from the cross-sectional area obtained for the same swatch the previous day. Five swatches were done for each of Examples 8–11 and the results were averaged together to obtain an average change in cross-sectional area (i.e., volume) after conditioning. The results are reported in Table II below.

TABLE II

| Example | Difference in Hair Cross-Sectional Area | Duncan Grouping |
|---|---|---|
| 8 | −2.309 | A |
| 9 | −3.417 | A |
| 10 | −4.185 | A |
| 11 | −8.156 | B |

Hair conditioners typically reduce hair volume and the negative number results in Table II show that all had some reduction in hair volume after treatment. The Duncan Grouping is a statistical analysis procedure which groups results together based upon the level of confidence chosen which, in this case, was a 95% confidence level. Under this analysis, Examples 8–10 had about the same level of conditioning effect at that confidence level while Example 11 was clearly statistically significantly different from the A group. Thus, Example 11 had more conditioning effect than the other three Examples tested.

The second test done was a combing force test using tresses of the above type which weighed 6 grams each and were between 10 and 12 inches in length (25.4–30.5 cm). tresses were wet with tap water, shampooed and again rinsed with tap water followed by application of 0.5 milliliters of one of the conditioners of Examples 8–11. The conditioner was worked into the hair swatch with the fingers and rinsed with $100°\pm 4°$ F. ($37.8°\pm 2.2°$ C.) tap water for 15 seconds, the swatch was squeezed between the fingers to remove the water, and detangled with a comb. The swatch was hung from a hook attached to a Shavitz 100 gram load cell connected to an analog-to-digital interface connected to a personal computer. The instrument was used to measure the average force resulting from combing the tress 10 consecutive times. The higher the average force reading, the more difficult it was to comb the hair and is thus an indication that less conditioning had taken place. Seven swatches were done per Example and the average results for each seven are summarized in Table III below.

TABLE III

| Example | Average Combing Force | Waller Grouping |
|---|---|---|
| 8 | 0.98286 | B |
| 9 | 1.11843 | A |
| 10 | 0.98314 | B |
| 11 | 0.81757 | C |

In Table III, the Waller-Duncan K-Ratio statistical analysis was used to evaluate whether the differences between readings were significant at a 95% confidence ratio. In this test, Example 9 (R' was decyl) was found to have a statistically significantly different and higher average combing force than Example B (R' was octyl) and Example 10 (R' was dodecyl). The lowest combing force was exhibited by swatches treated with Example 11 (R' was eicosyl: $C_{20}H_{41}$-) which was statistically significantly different from the others (Group C).

Examples 12–13

These Examples show the use of a polymethylalkylsiloxane of the present invention in a shampoo formulation.

Silicone XI was conventionally prepared by the platinum-catalyzed addition 1-octadecene to a trimethylsilyl-endblocked copolymer of dimethylsiloxane and methylhydridesiloxane units to obtain a polymer of the type shown in Formula I, supra, wherein R was a methyl group, R' was an octadecyl group, x had an average value of 240 and y had an average value of 60. The weight average molecular weight of the resulting polymer was 113,574 and it had a number average molecular weight of 3,323 with a peak molecular weight of 46,617. This polymer was a low to medium viscosity liquid at room temperature and had a melting transition as measured by the DuPont 910 Differential Scanning Calorimeter of 14.6° C.

A shampoo base composed of 750 parts of SIPON EA (ammonium laureth-3 sulfate at 28% actives from Alcolac, Inc. of Linthicum, Md.), 250 parts of SIPON L-22 (ammonium lauryl sulfate at 28% actives from Alcolac), 733.3 parts of deionized water, 5.20 parts of citric acid and 29 grams of ammonium chloride was prepared (hereinafter "Base 2").

Example 12 was prepared by dispersing 1 part of Silicone XI into 100 parts of Base 1 using the TEKMAR rotary mixer used in Examples 3–7. Example 13 was prepared by dispersing 2 parts of Silicone XI into 100 parts of Base 1 using the TEKMAR rotary mixer.

Two trained hair stylists shampooed one half of the head of hair of 16 women volunteer panelists with the shampoo of Example 12 and the other side with Example 13. The stylists were asked to complete an evaluation of the hair both wet and dry and after styling. Overall, both Examples 12 and 13 were found to have a positive conditioning effect on the hair, but Example 12 was preferred over Example 13, apparently because the higher level of Silicone XI in Example 13 provided too much conditioning. The Silicone XI left the hair soft without diminishing the clean feel which is expected after shampooing. One stylist verbally remarked that after rinsing, the hair had a squeaky clean feel, but instead of being difficult to style and comb as she had expected, the hair was very manageable.

Example 12 was rated as giving a higher level of fullness, body and bounce to the hair while Example 13 imparted a greater degree of shine to the hair and was easier to comb and detangle, both wet and dry, but felt more coated than the hair treated with Example 12. After styling, hair treated with Example 13 was judged to feel softer and more conditioned than that treated by Example 12 while Example 12 was judged to leave the hair more manageable.

Examples 14–17

In these Examples, the conditioning effect of four polymethylalkylsiloxanes was evaluated using a volunteer panel of 7 women and one man who were identified as having dry-hair or damaged hair such as from frequent hair dyeing, permanents, bleaching, chlorine from swimming pools, excess heat from hair styling appliances such as curling irons, etc.

Silicone XII was conventionally prepared by the platinum-catalyzed addition of a commercial mixture of 1-eicosene, 1-docosene and 1-tetracosene to a trimethylsilyl-endblocked copolymer of dimethylsiloxane and methylhydridesiloxane units to obtain a polymer of the type shown in Formula I, supra, wherein R was a methyl group, R' was an eicosyl, docosyl or tetracosyl group, x had an average value of 240 and y had an average value of 16. The weight average molecular weight of the resulting polymer was 78,048 and it had a number average molecular weight of 3,725 with a peak molecular weight of 25,919. This polymer was a liquid to a gel at room temperature and had a melting transition as measured by the DuPont 910 Differential Scanning Calorimeter of 18° C.

Silicone XIII was conventionally prepared by the platinum-catalyzed addition of a commercial mixture of 1-octadecene to a trimethylsilyl-endblocked copolymer of dimethylsiloxane and methylhydridesiloxane units to obtain a polymer of the type shown in Formula I, supra, wherein R was a methyl group, R' was an octadecyl group, x had an average value of 240 and y had an average value of 16. The weight average molecular weight of the resulting polymer was 40,104 and it had a number average molecular weight of 3,311 with a peak molecular weight of 20,485. This polymer was a medium viscosity liquid at room temperature and had a melting transition as measured by the DuPont 910 Differential Scanning Calorimeter of −5° C.

The conditioner formulation used a base composed of 2 parts cetyl alcohol, 0.7 parts ADOGEN® 432ET, 0.05 parts citric acid, 0.4 parts SCHERCODINE® S, 0.4 parts tricetyl amine, 0.032 parts KATHON® CG, and 96.418 parts deionized water (hereinafter "Base 3"). Examples 14, 15, 16 and 17, respectively, were prepared by adding 1% of Silicone XII, XIII, XI and V, respectively to a portion of Base 3 using a high shear mixer.

Each of the four conditioner formulations (Example 14–17) were applied by the panelists in their homes to their entire head of hair after shampooing. Each formulation was evaluated for a one week period before the panelist was given a new formulation to test. The panelist also completed an evaluation form before being given another formulation to test.

Overall, the expected attributes of combing ease, soft feel and conditioning were observed by the panelists for each of Examples 14–17. Additionally, the treated hair was judged overall to have the desirable characteristics of fullness, body, shine, manageability and a clean look without the conditioner being judged as imparting a coated feel to the hair, weighing the hair down or leaving a matted/flat look. The latter was found to vary depending upon the specific polymethylalkylsiloxane. Overall, flyaway is typically noted as being a problem when polydimethylsiloxanes are used, but was not perceived to be a problem from the ratings given to the compositions tested.

One conclusion drawn from the results of this study is that for users with dry or damaged hair, a polymethylalkylsiloxane with larger amounts of R' groups such as Siloxane XI is preferred. For other hair types such as normal or oily hair, this type of polymethylalkylsiloxane may tend to leave the hair more coated and weighed down in appearance when it is used.

Example 17 containing Silicone V was rated very high in panelist number scale ratings and in voluntary comments submitted by the panelists. This polymer was rather high in molecular weight relative to the other silicone polymers tested.

From the results, a more ordered structure for the polymethylalkylsiloxanes of the present invention, as evidenced by higher viscosity or gelation, appears to be desirable from a conditioning performance standpoint. Example 15 contains Silicone XIII which is a medium viscosity liquid with 18 carbon atom R' groups. Example 14 contained Silicone XII which has the same silicone polymer backbone as in Example 15, but was a liquid to a gel with 20-24 carbon atom R' groups and received higher ratings for performance than did Example 15.

Improved manageability of the hair was seen for Examples 14-17, but was especially noticeable for Example 17, the highest molecular weight polymer tested. Manageability is thought to result because the silicone polymer chains yield readily under a high force such as combing, but under lower forces, such as a light wind or normal head movement, they do not allow the hairstyle to relax.

Examples 18-22

In these Examples, a level study was conducted using the formulation listed in Table I wherein the Silicone I was omitted and replaced by the same amount of water in the formulation (comparative Example 18). The remaining Examples were prepared with Silicone XII added at 0.1% (Example 19), 0.5% (Example 20), 1.0% (Example 21) and 2.0% (Example 22), respectively, levels to Base 1. The study was done to determine if differences could be observed among the various levels of polymethylalkylsiloxanes used as well as between Examples 19-22 and comparative Example 18.

In this evaluation, 100 volunteer panelists aged from 18-55 participated in the testing which was conducted by trained hair stylists over a 4 day period. A "half-head" procedure of the type described in the previous Examples was used with a random selection of two compositions to be applied, after the hair was shampooed, to each one half of the panelist's hair in an amount of up to 7.5 milliliters of product per side. The stylists and panelists were not told the identity of any of the compositions being tested. The hair stylists rotated to a new panelist after application of the compositions and rinsing.

The panelists were asked to complete a 9 point interval evaluation containing statements of the types noted in the above Examples while the hair stylists were asked to complete a 60 point structured line scale containing statements which were ranked according to an assigned point scale.

The results were that while there was a difference between Example 18 with no polymethylalkylsiloxane and Examples 19-22, there were few differences noted between Examples 19-22. An important difference between Example 18 and Examples 19-22 was that Example 18 contained a significant amount of four different organic hair conditioning agents while Base 1 only contained 1% of one organic hair conditioning agent plus the polymethylalkylsiloxane.

Overall, the panelists perceived Example 19 to leave the hair feeling drier and less conditioned than did Examples 21 or 22. Example 18 was judged to leave the hair with a cleaner look than Examples 19, 21 and 22, and left the hair with more shine than did Examples 19 and 21. Examples 19-22 were judged to have a thinner consistency and to impart less lubricity to the hair than did Example 18. The stylists rated Example 20 to be easier to rinse out of the hair than were Examples 18 and 19. After one day, hair treated with Example 18 was judged to have a less clean feel than hair treated with Examples 19-22. Thus, Examples 19-22 were fairly comparable with a conventional hair conditioner formulation (Example 18) with multiple hair conditioning agents.

Examples 23-26

Since few differences were noted in the study done with Examples 18-22, another study was done using the same conditioner base throughout so that any conditioning effects due to the presence of the polymethylalkylsiloxane would become more apparent.

This level study was conducted using Base 1 alone (comparative Example 23) and with Silicone XII added at 0.5% (Example 24), 2.0% (Example 25) and 5.0% (Example 26) levels, respectively, to Base 1 using the TEKMAR ® rotary mixer used in Examples 3-7.

The study was conducted over 5 days using 115 volunteer panelists aged 18-55 in the same manner as described in Examples 18-22 above, but with Examples 23-26.

The results of the study were that significant differences between Examples 24-26 with the three different levels of Silicone XII and comparative Example 23 were observed. Both the stylists and the panelists judged that the addition of the polymethylalkylsiloxane to Base 1 provided a wet and dry hair combing advantage. Examples 25 and 26 were rated as providing a less dry and more conditioned feel to the hair than was provided by Examples 23 or 24. A more coated feel to the hair after drying was observed with increasing amounts of polymethylalkylsiloxane and this was judged as being especially noticeable with Example 26.

The stylists rated Examples 25 and 26 as having a thinner consistency, as being more easily distributed through the hair, but less easily rinsed out than Example 23. One day after the hair was treated, the panelists felt that: Example 24 tended to leave the hair less matted than did Example 23; Example 26 was felt to leave the hair easier to comb than did Example 23; and Example 23 had a less dry feel on the hair relative to the feel of hair treated with Examples 24 or 26.

Example 26

This Example illustrates a preferred shampoo formulation using the present invention having good stabilization of the polymethylalkylsiloxane in the shampoo.

The shampoo formulation consists of two parts with a range of each ingredient being given in parentheses after the nominal amount in parts by weight listed first (all ingredients are on a 100% solids basis):

Part I is Cetyl/Stearyl Alcohol in a 60/40 weight:weight ratio, 1% (0.5-16%); Silicone XI, 2% (0.1-3%); and Coco-Betaine, 1.8 (8-12% of the total surfactant present).

Part II is Ammonium Lauryl Sulfate/Ammonium Lauryl Ether-3 Sulfate in an 80/20 weight:weight ratio, 16.2% (14-22%); Cetyltrimethylammonium Chloride, 0.5% (0.1-0.7%); and deionized water, 78.5% (balance to 100%).

The shampoo formulation of Example 27 is prepared by melting the Cetyl/Stearyl Alcohol together with the Silicone XI until a homogeneous melt is obtained. The Coco-Betaine is then added on top of the melt (without mixing) after the melt is cooled to room temperature to thereby obtain Part I.

The water and Cetyltrimethylammonium Chloride are then mixed together followed by the sulfate surfactant mixture. The mixture is allowed to stir at room temperature until it becomes clear to complete preparation of Part II.

Part II is then heated to 70° C. with stirring. Part I is gently remelted until it becomes fluid and Part II is then poured into Part I with stirring using the TEKMAR RW20 DZM stirrer. The temperature is kept at 70° C. to allow the ingredients to mix well with vigorous stirring and then the heat source is removed and the formulation is allowed to cool to room temperature while vigorous stirring is maintained. The resulting formulation is Example 27.

A shampoo formulation was prepared by this method and the formulation had a Brookfield viscosity of 6,000 centipoise at 30 R.P.M., #4 spindle after 30 seconds at room temperature.

Example 28

This Example illustrates an aqueous emulsion carrier for delivering polymethylalkylsiloxanes from a pump spray container for use as a pump spray hair conditioner.

Example 28 was prepared by slowly adding 3.00 grams of PEMULAN ® TR-2 (Acrylates/C10-30 Alkyl Acrylate Crosspolymer) from B.F. Goodrich Group, Specialty Polymers & Chemicals of Cleveland, Ohio) to 2912.0 grams of double distilled water with moderate stirring using the TEKMAR RW20 DZM rotary stirrer. After the majority of the PEMULAN ® TR-2 appeared to be hydrated (only a few small clumps were apparent), 24.00 grams of triethanolamine was added to the stirring mixture. Stirring was continued until only one piece of undispersed PEMULAN ® TR-2 remained. Stirring was stopped and the resulting intermediate composition was allowed to remain at room temperature overnight.

On the next day, the intermediate composition was stirred for 15–20 minutes and no remaining undispersed PEMULAN ® TR-2 was observed.

A solution containing 30.0 grams of Silicone I, 30 grams of General Electric SF-1202 Silicone Fluid and 1.0 gram of fragrance was prepared and slowly poured into the intermediate composition with moderate stirring. When the solution was completely added, the stirring rate was increased to create a small vortex.

To prepare a better emulsion, 300 milliliters of the resulting composition was sheared using the ULTRA-TURRAX ® T50 rotary mixer used in Example 1 at 3,500–4,000 R.P.M. The resulting emulsion (Example 28) was placed in a conventional pump spray bottle and sprayed onto the hair of models as a conditioner with good results.

Examples 29–40

In these examples, the wet combing characteristics of alkylsiloxanes containing several different R' groups as well as different silicone polymer backbones were compared against themselves and against a control which was Base 1 used in Examples 3–7. Examples 29, 30, 33, 34 and 37–39 were comparative examples. The wet combing characteristics were measured as described in Examples 8–11 for the combing force test summarized in Table III.

Examples 29, 33 and 37 were Base 1 only and the remaining Examples were prepared by adding 0.5% of the polymethylalkylsiloxane being tested to Base 1. Example 30 was a batch of Silicone VIII where R' was a $C_{10}$ group and no melting point transition was detected. Example 31 was Silicone XIV which was prepared in the same manner as described for Silicone IX, but by adding 1-dodecene to a prepolymer of the type shown in Formula I, supra, where R' was a methyl group, x had an average value of 50, y had an average value of 36, R' was hydrogen, and the number average molecular weight was 5824. The resulting Silicone XIV had a melting point transition at −55° C. Examples 32 and 36 were Silicone I where R' was a $C_{18}$ group. Example 34 was Silicone VII. Example 35 was Silicone XV which was a medium to high viscosity liquid copolymer of the type described in Formula I, supra, where R' was a methyl group, x had an average value of 300, y had an average value of 48, R' was a $C_{18}$ group, the melting transition was 7.9° C., had a number average molecular weight of 2,798 and a weight average molecular weight of 73,147. Example 38 was Silicone XVI which was made by adding 1-octene to the prepolymer used to prepare Silicone XIV and the resulting polymer had a melting point transition of −104° C. Example 39 was Silicone XVII which was made by adding 1-decene to the prepolymer used to prepare Silicone XIV and the resulting polymer had a melting point transition of −67° C. Example 40 was Silicone IX and no melting point transition was detected for this polymer.

The wet combing tests were done in three separate groups and are summarized in Table IV below.

TABLE IV

| Example | R' | Average Wet Combing Force | Waller Grouping |
|---------|------|-------|---|
| 29 | — | 1.5140 | A |
| 30 | $C_{10}$ | 1.0437 | B |
| 31 | $C_{12}$ | 1.0169 | B |
| 32 | $C_{18}$ | 0.7727 | C |
| 33 | — | 1.4137 | A |
| 34 | $C_8$ | 0.9164 | B |
| 35 | $C_{18}$ | 0.7203 | C |
| 36 | $C_{18}$ | 0.7384 | C |
| 37 | — | 1.5110 | A |
| 38 | $C_8$ | 1.1126 | B |
| 39 | $C_{10}$ | 0.9809 | B |
| 40 | $C_{12}$ | 0.9911 | B |

From Table IV, it is apparent that the polymethylalkylsiloxanes with $C_{18}$ as the R' group are clearly better in conditioning effect than the control or the other polymers. Even though different silicone polymer backbones were used, the general trend is that conditioning of the hair, as measured by a reduction in average wet combing force, increases as the length of the R' group present is increased.

What we claim is:

1. An improved composition for treating the hair comprising a hair conditioning agent dispersed within a cosmetically acceptable carrier medium wherein the improvement comprises inclusion of from about 0.1% to about 10% by weight of a polymethylalkylsiloxane as at least one of the hair conditioning agents, based upon the total weight of the agents and carrier medium, wherein the polymethylalkylsiloxane has the average formula

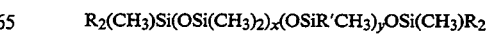

$$R_2(CH_3)Si(OSi(CH_3)_2)_x(OSiR'CH_3)_yOSi(CH_3)R_2$$

wherein each R is selected from the group consisting of methyl) ethyl and phenyl groups, R' is an alkyl group of from 8 to about 60 carbon atoms where the total number of R' groups present has an average of at least 12 carbon atoms, the values of x and y are such that the ratio of x:y is in the range of from 97:3 to 55:45, the sum of $x+y$ is greater than or equal to about 60 and less than or equal to about 1,333 and the polymethylalkylsiloxane has a melting transition, as measured by a differential scanning calorimeter, between about $-25°$ C. to $+27°$ C.

2. The composition as claimed in claim 1 wherein the sum of $x+y$ is greater than or equal to about 250 and less than or equal to about 800.

3. The composition as claimed in claim 2 wherein R is a methyl group, and R' is a linear alkyl group of from 16 to 24 carbon atoms.

4. The composition as claimed in claim 3 wherein the ratio of x:y is from 96:4 to 80:20 and the polymethylalkylsiloxane hair conditioning agent is from about 0.1%–5% by weight of the composition.

5. The composition as claimed in claim 3 wherein the ratio of x:y is from 97:3 to 93:7 and the polymethylalkylsiloxane hair conditioning agent is from about 0.1%–5% by weight of the composition.

6. The composition as claimed in claim 3 wherein the ratio of x:y is from 88:12 to 80:20 and the polymethylalkylsiloxane hair conditioning agent is from 0.10 to 5% by weight of the composition.

7. The composition as claimed in claim 1 wherein the polymethylalkylsiloxane hair conditioning agent is from 0.5% to 7% by weight of the composition.

8. The composition as claimed in claim 1 wherein the carrier medium is a hair shampoo.

9. The composition as claimed in claim 1 wherein the carrier medium is a hair conditioner.

10. The composition as claimed in claim 1 wherein the carrier medium is an aerosol spray carrier medium.

* * * * *

UNITED STATES PATENT AND TRADEMARK OFFICE
CERTIFICATE OF CORRECTION

PATENT NO. : 5,393,521
DATED : February 28, 1995
INVENTOR(S) : Lance-Gomez et al.

It is certified that error appears in the above-identified patent and that said Letters Patent is hereby corrected as shown below:

On the title page, item [57] Abstract, lines 1-5:
In the Abstract, change the first sentence from "These improved compositions include a polymethylakylsioxane hair conditioning These improved compositions include a polymethyMcarrier medium such as a hair shampoo, hair conditioner or aerosolspray composition." to --These improved compositions include a polymethylalkylsiloxane hair conditioning agent dispersed in a cosmetically acceptable carrier medium such as a hair shampoo, hair conditioner or aerosol spray composition.--;

In column 8 at line 17 change "preferred is. 0.5-2.5%" to
--preferred is 0.5-2.5%--;

In column 12 at line 54 change "#or" to --for--;

UNITED STATES PATENT AND TRADEMARK OFFICE
CERTIFICATE OF CORRECTION

PATENT NO. : 5,393,521

DATED : February 28, 1995

INVENTOR(S) : Lance-Gomez et al

It is certified that error appears in the above-indentified patent and that said Letters Patent is hereby corrected as shown below:

In column 18 at line 45 change "Example 26" to --Example 27--.

Signed and Sealed this

First Day of August, 1995

Attest:

BRUCE LEHMAN

Attesting Officer     Commissioner of Patents and Trademarks